(12) United States Patent
Speidel et al.

(10) Patent No.: US 9,652,862 B1
(45) Date of Patent: May 16, 2017

(54) SYSTEM AND METHOD FOR DYNAMIC DEVICE TRACKING USING MEDICAL IMAGING SYSTEMS

(71) Applicant: Wisconsin Alumni Research Foundation, Madison, WI (US)

(72) Inventors: Michael Speidel, Madison, WI (US); Charles Hatt, Milwaukee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/921,891

(22) Filed: Oct. 23, 2015

(51) Int. Cl.
| | |
|---|---|
| G06K 9/00 | (2006.01) |
| G06T 7/20 | (2017.01) |
| G06T 7/00 | (2017.01) |
| G06T 11/00 | (2006.01) |

(52) U.S. Cl.
CPC ........ *G06T 7/2046* (2013.01); *G06K 9/00208* (2013.01); *G06T 7/0012* (2013.01); *G06T 7/0046* (2013.01); *G06T 11/006* (2013.01); *G06T 2207/10028* (2013.01); *G06T 2207/10121* (2013.01); *G06T 2207/20081* (2013.01); *G06T 2211/421* (2013.01)

(58) Field of Classification Search
None
See application file for complete search history.

(56) References Cited

U.S. PATENT DOCUMENTS

| | | | |
|---|---|---|---|
| 2008/0137923 A1 | 6/2008 | Spahn | |
| 2010/0121181 A1* | 5/2010 | Wang | ........................ A61B 6/12 600/424 |
| 2012/0296202 A1 | 11/2012 | Mountney et al. | |
| 2013/0177230 A1 | 7/2013 | Feng et al. | |
| 2013/0303890 A1* | 11/2013 | Duindam | ................ A61B 5/00 600/424 |

(Continued)

FOREIGN PATENT DOCUMENTS

| | | |
|---|---|---|
| DE | 102012224057 A1 | 6/2014 |
| WO | 2016131955 A1 | 8/2016 |

OTHER PUBLICATIONS

Brost, et al., Respiratory Motion Compensation by Model-Based Catheter Tracking During EP Procedures, Medical Image Analysis, 2010, 14(5):695-706.

(Continued)

*Primary Examiner* — Weiwen Yang
(74) *Attorney, Agent, or Firm* — Quarles & Brady, LLP

(57) ABSTRACT

A system and method are provided for generating images that track a position and shape of a medical device within a subject. The method includes acquiring image data from a subject along at least two disparate view angles, each view angle including a deformable medical device arranged in the subject. The method also includes receiving images reconstructed from the image data and exploring a search space to compare the images with a dynamic three-dimensional (3D) model at least using a deformation parameter to determine a position and shape of the deformable medical device within the subject. The method further includes displaying an image of the subject and deformable medical device arranged within the subject based on the position and shape of the deformable medical device within the subject.

20 Claims, 7 Drawing Sheets

(56) References Cited

U.S. PATENT DOCUMENTS

2013/0324833 A1* 12/2013 Barley ............... A61B 5/6876
600/409
2014/0235999 A1* 8/2014 Birkenbach ........ A61B 19/5244
600/424

OTHER PUBLICATIONS

Gall, et al., Hough Forests for Object Detection, Tracking and Action Recognition, IEEE Transactions on Pattern Analysis and Machine Intelligence, 2011, 11(33):2188-2202.
Hatt, et al., Robust 5DOF Transesophageal Echo Probe Trackino at Fluoroscopic Frame Rates, International Conference on Medical Image Computing and Computer-Assisted Intervention, 2015, pp, 290-297.
Hatt, et al., Hough Forests for Real-Time, Automatic Device Localization in Fluoroscopic Images: Application to TAVR, International Conference on Medical Image Computing and Computer-Assisted Intervention, 2015, pp. 307-314.
Hatt, et al., Dynamic Tracking of Prosthetic Valve Motion and Deformation from Bi-Plane X-ray Views: Feasibility Study, Proc. SPIE Int. Soc. Opt. Eng., 2016, 9786.
PCT International Search Report and Written Opinion, PCT/US2016/057694, Jan. 30, 2017.

* cited by examiner

SYSTEM AND METHOD FOR DYNAMIC DEVICE TRACKING USING MEDICAL IMAGING SYSTEMS

CROSS-REFERENCE TO RELATED APPLICATIONS

N/A

BACKGROUND

The present disclosure is directed to systems and methods for tracking interventional or implantable medical devices using medical imaging systems. More particularly, the disclosure relates to a system and method for visualizing medical devices during an implantation or interventional procedure, for example, as the medical devices are adjusted and changed during the procedure.

Image-based guidance of therapeutic devices, such as catheters, and/or the placement of interventional devices, such as guidewires and stents is a key component of modern medicine. Currently, x-ray fluoroscopy is the gold standard for such image-guided procedures. For example, the tips of guidewires can be easily visualized using conventional x-ray fluoroscopy by applying small, radio-opaque markers to the tips.

However, as the device becomes more complex and/or the surrounding tissue exerts greater influence on a system, it can be difficult to communicate the desired information to a clinician. For example, guiding and placing an expandable stent within a vessel can be difficult using traditional methods of visualization using x-ray fluoroscopy because the stent, itself, is a three-dimensional object, can move in three-dimensions, and can deform in various directions during movement or deployment when interacting with surrounding tissue. Thus, it can be very difficult for a clinician to accurately understand the orientation and deployment position of the stent in three dimensions from a two-dimensional, fluoroscopic image.

Transcatheter aortic valve replacement (TAVR) has been developed as a less-invasive treatment option for patients with severe aortic valve stenosis who are high risk for open chest surgery. In this fluoroscopically-guided procedure, a balloon-expandable stent-supported tissue valve is carefully positioned in the left ventricular outflow tract at the level of the aortic annulus. The balloon is expanded to deploy the valve. Accurate device visualization relative to the target anatomy is both highly challenging and critical to procedure success.

Conventional x-ray fluoroscopic imaging only provides a 2D view of a 3D device, leading to ambiguities in the position and orientation of the device. Continuous high frame rate 3D CT scanning of the device in the interventional catheter laboratory is not practical and the radiation dose to the patient would prohibit its use for visualization during such a procedure. Back-projection reconstruction from 2 simultaneous bi-plane views may be suitable for very simple devices such as a curvilinear guidewire or catheter body, but for complex devices that are self-overlapping in the measured x-ray views, such as a TAVR valve, these traditional imaging processes fail.

Accordingly, multimodal image fusion has gained interest, particularly for cardiac interventional procedures. For example, catheter detection and tracking using fluoroscopy can provide motion compensation of anatomical roadmaps used to help guide electrophysiology procedures, such as described in Brost, Alexander, et al. "Respiratory motion compensation by model-based catheter tracking during EP procedures." Medical Image Analysis 14.5 (2010): 695-706. To provide the clinician with more information in structural heart interventions, transesophageal echo (TEE) has been registered with x-ray fluoroscopic (XRF) images. This TEE/XRF registration allows anatomical information from echo to be combined with device imaging from XRF and help the clinician to better understand the position and deployment condition of a complex device, such as an expandable stent or the like. However, these registration systems do not provide an XRF-based 3D representation of the device registered to TEE, making it difficult to fully appreciate the device status relative to patient anatomy.

Therefore, it would be desirable to have new systems and methods that enable a clinician to track and understand the position and movement of interventional and/or implantable medical devices during an interventional procedure.

SUMMARY

The present disclosure overcomes the aforementioned drawbacks by providing a system and method generating images that track a position and shape of a deformable medical device within a subject. The system and method include acquiring image data from a subject along at least two disparate view angles, each view angle including a deformable medical device arranged in the subject. The system and method also include receiving images reconstructed from the image data and exploring a search space to compare the images with a dynamic three-dimensional (3D) model at least using a deformation parameter to determine a position and shape of the deformable medical device within the subject. The system and method further include displaying an image of the subject and deformable medical device arranged within the subject based on the position and shape of the deformable medical device within the subject.

In accordance with one aspect of the disclosure, a method is provided for generating images that track a position and shape of a deformable medical device within a subject. The method includes (i) receiving image data acquired from the subject along at least two disparate view angles, each view angle including a deformable medical device arranged in the subject. The method also includes (ii) accessing a three-dimensional (3D) model including the deformable medical device that includes a deformation parameter for the deformable medical device and (iii) exploring a search space including the deformation parameter to match the image data with the 3D model within a predetermined tolerance to determine a position and shape of the deformable medical device. The method also includes using the image data and the position and shape of the deformable medical device determined in (iii) to display an image of the deformable medical device arranged within the subject.

In accordance with another aspect of the disclosure, a system is provided for generating images that track a position and shape of a medical device within a subject. The system includes an x-ray imaging system configured to acquire image data from a subject along at least two disparate view angles, each view angle including a deformable medical device arranged in the subject. The system also includes a reconstruction system configured to reconstruct images of the subject and deformable medical device from the image data and a computer system configured to receive the images and explore a search space to compare the images with a dynamic three-dimensional (3D) model at least using a deformation parameter to determine a position and shape of the deformable medical device within the subject. The system also includes a display configured to display an image of the subject and deformable medical device arranged within the subject based on the position and shape of the deformable medical device within the subject determined by the computer system.

In accordance with yet another aspect of the disclosure, a system is provided for generating images that track a position and shape of a medical device within a subject. The system includes an image processing system configured to (i) receive image data acquired from the subject along at least two disparate view angles, each view angle including the medical device. The image processing system is further configured to (ii) access a three-dimensional (3D) model including the medical device that includes a deformation parameter for the medical device and (iii) explore a search space including the deformation parameter to match the image data with a forward-projection of the 3D model within a predetermined tolerance to determine a position and shape of the medical device. The image processor is further configured to, using the image data and the position and shape of the medical device determined in (iii), display an image of the medical device arranged within the subject.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1A:
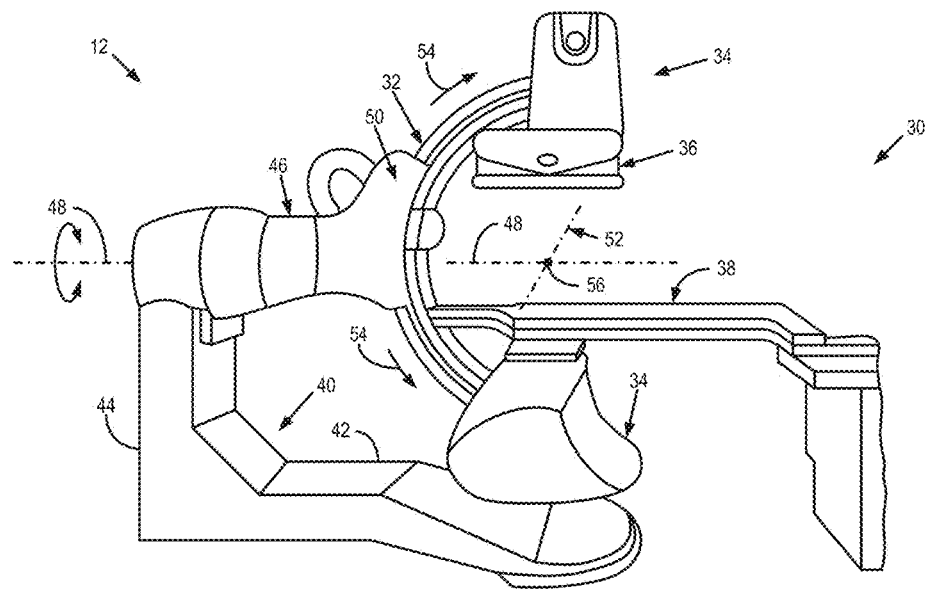
FIG. 1A is a perspective view of an example of an x-ray imaging system that can be used in accordance with the present disclosure to track medical devices.
Figure 1B:
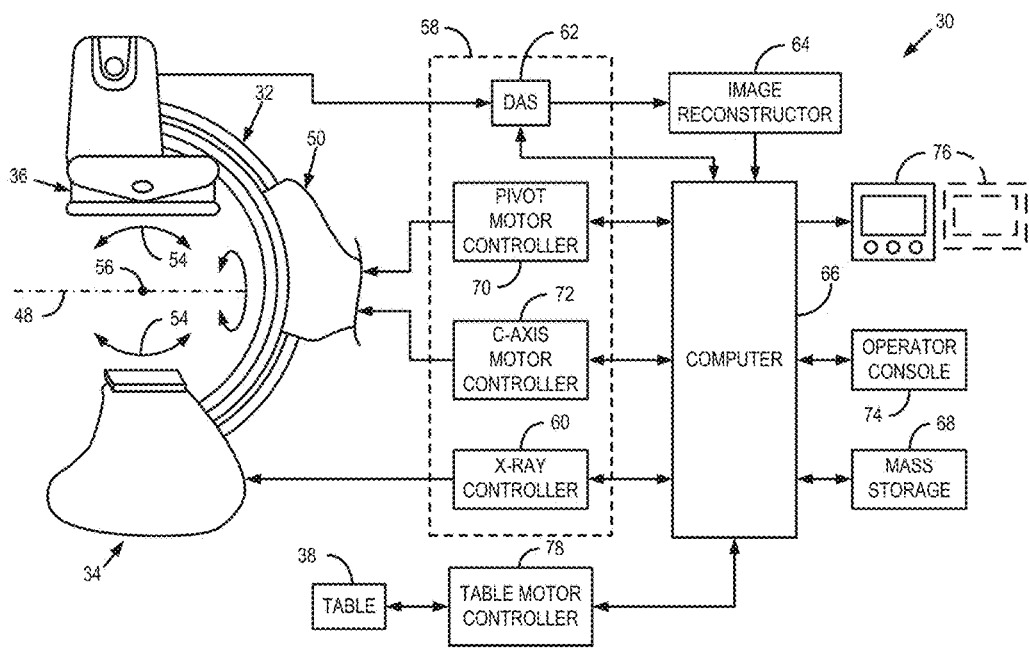
FIG. 1B is a block diagram of the system of FIG. 1A.

Referring to FIGS. 1A and 1B, an example of an imaging system 12 is provided. The imaging system 12 may be a bi-plane x-ray imaging system or other x-ray fluoroscopic (XRF) imaging system. The x-ray imaging system 30 is illustrated as a so-called "C-arm" imaging system; however, other geometries may be used to acquired x-ray images. For example, in many clinical settings it is desirable to use a bi-plane system, instead of the single C-arm system illustrated in FIGS. 1A and 1B. Such bi-plane systems may be particularly desirable to enable simultaneous acquisition of images along orthogonal view angles, such as in the presence of patient or physiological motion. However, any of a variety of x-ray imaging systems capable of acquiring image data may be used, including systems that acquire images using a single plane x-ray system. FIGS. 1A and 1B illustrate a single plane system to avoid the additional illustration complexity of an additional C-arm; however, one of ordinary skill in the art will readily appreciate that bi-plane and other imaging systems are available and will be described herein.

The imaging system 30, as illustrated, may be generally designed for use in connection with interventional procedures. The imaging system 30 is characterized by a gantry 32 forming a C-arm that carries an x-ray source assembly 34 on one of its ends and an x-ray detector array assembly 36 at its other end. In a bi-plane system, a second x-ray source (not illustrated for clarity in the drawing) and detector array assembly (also, not illustrated for clarity in the drawing) are included. Whether there is one or a multitude of C-arms, each gantry 32 enables the x-ray source assembly 34 and detector array assembly 36 to be oriented in different positions and angles around a patient disposed on a table 38, while enabling a physician access to the patient.

The gantry includes a support base 40, which may include an L-shaped pedestal that has a horizontal leg 42 that extends beneath the table 38 and a vertical leg 44 that extends upward at the end of the horizontal leg 42 that is spaced from of the table 38. A support arm 46 is rotatably fastened to the upper end of vertical leg 44 for rotation about a horizontal pivot axis 48. The pivot axis 48 is aligned with the centerline of the table 38 and the support arm 46 extends radially outward from the pivot axis 48 to support a drive assembly 50 on its outer end. The C-arm gantry 32 is slidably fastened to the drive assembly 50 and is coupled to a drive motor (not shown) that slides the C-arm gantry 32 to revolve it about a C-axis 52, as indicated by arrows 54. The pivot axis 48 and C-axis 52 intersect each other at an isocenter 56 that is located above the table 408 and they are at disparate view angels, such as perpendicular to each other.

The x-ray source assembly 34 is mounted to one end of the C-arm gantry 32 and the detector array assembly 36 is mounted to its other end. As will be discussed in more detail below, the x-ray source assembly 34 includes an x-ray source (not shown) that emits a beam of x-rays, which are directed at the detector array assembly 36. Both assemblies 34 and 36 extend radially inward to the pivot axis 38 such that the center ray of this cone beam passes through the system isocenter 56. The center ray of the x-ray beam can, thus, be rotated about the system isocenter 56 around either the pivot axis 38, the C-axis 52, or both during the acquisition of x-ray attenuation data from a subject placed on the table 38.

As mentioned above, the x-ray source assembly 34 contains an x-ray source that emits a beam of x-rays when energized. The center ray passes through the system isocenter 56 and impinges on a two-dimensional flat panel digital detector housed in the detector assembly 36. Each detector element produces an electrical signal that represents the intensity of an impinging x-ray and, hence, the attenuation of the x-ray as it passes through the patient. During a scan, the x-ray source and detector array can be rotated about the system isocenter 56 to acquire x-ray attenuation projection data from different angles.

Figure 2A:
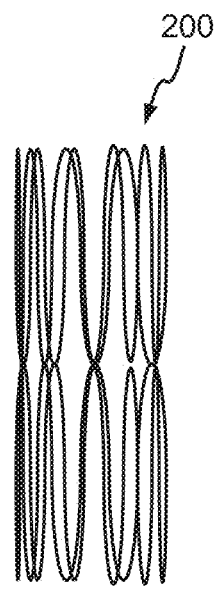
FIG. 2A is an illustration of a deformable medical device in a first, non-deployed state.
Figure 2B:
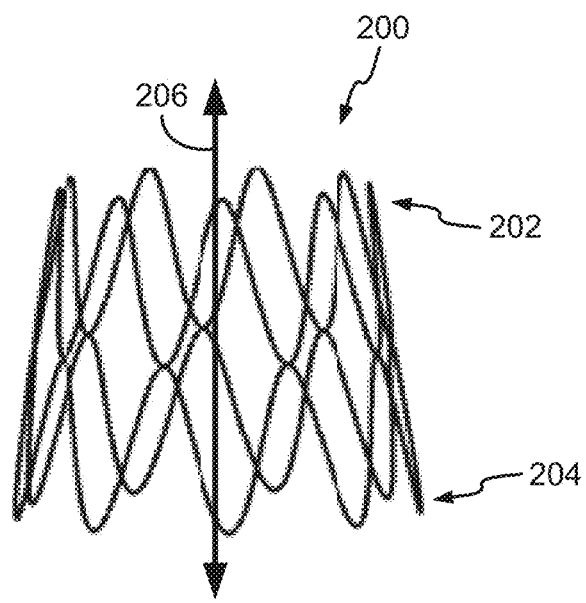
FIG. 2B is an illustration of the deformable medical device of FIG. 2A in a second state.

Referring particularly to FIG. 2B, the rotation of the assemblies 34 and 36 and the operation of the x-ray source are governed by a control system 58 of the imaging system 30. The control system 58 includes an x-ray controller 60 that provides power and timing signals to the x-ray source. A data acquisition system (DAS) 62 in the control system 58 samples data from detector elements in the detector array assembly 36 and passes the data to an image reconstructor 64. The image reconstructor 64, receives digitized x-ray data from the DAS 62 and performs image reconstruction. The image reconstructed by the image reconstructor 64 is applied as an input to a computer 66, which stores the image in a mass storage device 68 or processes the image further.

The control system 58 also includes pivot motor controller 70 and a C-axis motor controller 72. In response to motion commands from the computer 66, the motor controllers 70 and 72 provide power to motors in the imaging system 30 that produce the rotations about the pivot axis 38 and C-axis 52, respectively. A program executed by the computer 66 generates motion commands to the motor controllers 70 and 72 to move the assemblies 34 and 36 in a prescribed scan path.

The computer 66 also receives commands and scanning parameters from an operator via a console 74 that has a keyboard and other manually operable controls. An associated display 76 or displays allows the operator to observe the reconstructed image and other data from the computer 66. The operator supplied commands are used by the computer 66 under the direction of stored programs to provide control signals and information to the DAS 62, the x-ray controller 60, and the motor controllers 70 and 72. In addition, the computer 66 operates a table motor controller 78, which controls the patient table 408 to position the patient with respect to the system isocenter 56.

Existing attempts to perform 3D/2D registration and tracking using imaging systems assume that the device being tracked is a rigid, static object with a shape that has been fully characterized prior to x-ray imaging (e.g. through a calibration CT scan, or from CAD drawings). For example, the Philips Healthcare has attempted to provide products that perform 3D/2D registration and tracking under the name EchoNavigator. These and similar systems perform 3D/2D registration by estimating the pose of a rigid, transesophageal echo probe. Unfortunately, these systems do not provide accurate 3D representations of a catheter or similar device that changes shape and deforms as it is deployed inside the patient. That is, these systems cannot accurately track deformable medical devices.

Accordingly, improved tracking and visualization methods are needed, for example, to guide procedures such as TAVR valve procedures and the like. Consider, as a non-limiting example, the expandable frame 200 of a TAVR valve illustrated in an unexpanded or undeployed state in FIG. 2A. In the unexpanded state illustrated in FIG. 2A, the expandable frame 200 may take a generally-cylindrical shape. However, the expandable frame 200 and, thus, the TAVR valve during and after deployment, is not a rigid body and deforms. As a general example, when deployed or during deployment, the expandable frame 200 may take a variety of shapes, including a truncated cone having a trapezoidal longitudinal cross section, such as illustrated in FIG. 2B. In the shape illustrated in FIG. 2B, the expandable frame 200 extends from a first diameter at a first end 202 to a second diameter at a second end 204. This generally-trapezoidal shape of the expandable frame 200 is only one of many shapes that the expandable frame 200 may assume. For example, even with the example illustrated in FIG. 2B, the first diameter at the first end 202 to a second diameter at the second end 204 may vary independently, thereby presenting an extensive number of potential shapes for the expandable frame 200.

The present disclosure provides systems and methods that can leverage imaging systems, such as described above with respect to FIGS. 1A and 1B to obtain frame-by-frame 3D representations of an interventional device that changes shape and deforms as it is deployed inside the patient (e.g. a balloon-mounted prosthetic valve, in a TAVR procedure), using the 2 x-ray views available in an interventional bi-plane or similar imaging system.

As will be described, the present disclosure resolves challenges of accurately tracking and communicating moving/expanding or deforming interventional devices using a pose estimation technique. The method compares measured x-ray images to forward projections of a "dynamic" 3D model, which can assume different states of expansion and deformation. The state of expansion/deformation is defined by a set of deformation parameters that are included in the search space explored when optimizing the similarity between forward projections and x-ray images. In one configuration, the search space includes deformation parameters that include the position, pitch, yaw, roll, proximal diameter, and distal diameter of the device. That is, the search space may include rigid parameters, such as position, pitch, yaw, and roll that are coupled with additional parameters, such as proximal diameter, and distal diameter of the device or other parameters that, together, describe the position and deformation of the device. The present disclosure may additionally exploit a priori knowledge to limit the search space. Specifically, when applicable, a priori knowledge that the device is initially in its un-deployed state or has entered a deployed state may be used to restrict the search space.

For example, in the case of an expandable interventional device, such as a TAVR or other balloon-expanded device, the a priori knowledge may be that the deformable device undergoes predictable changes in shape, which can be characterized in a calibration step. Some additional examples of a priori knowledge include the position, orientation, and shape in the current time frame relative to a prior time frame because the current time frame should be similar to the position, orientation, and shape determined in the previous time frame. Using this a priori knowledge makes the search more efficient and helps the search converge to the correct answer. Another example of a priori knowledge relates to certain device shapes that may be "unphysical." That is, it may be known that the device does not turn itself inside out or assume a shape that is not practical when deployed.

Figure 3:
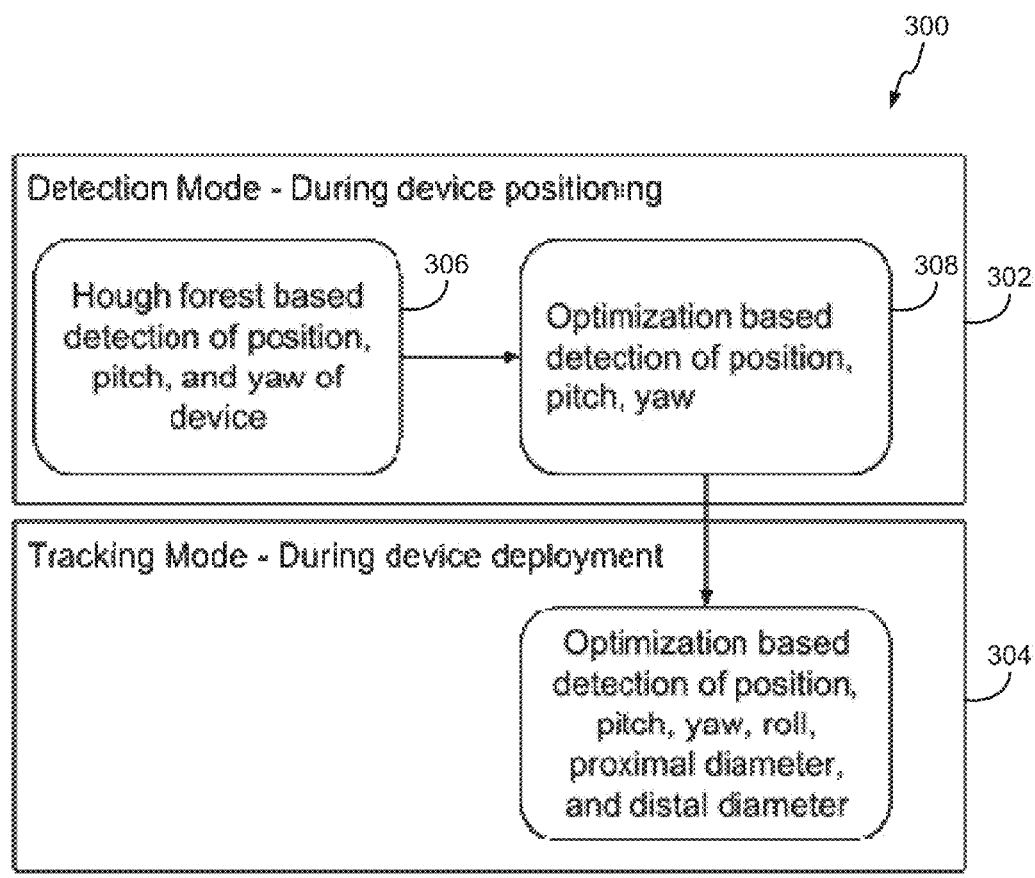
FIG. 3 is a flow chart setting forth examples of steps for tracking a medical device in accordance with the present disclosure.

For example, referring to FIG. 3, example steps 300 of a process for performing a 3D pose estimation of a dynamic or deformable medical device, such as a artificial valve, are illustrated. The process can be conceptualized as being formed of two sub-processes including a detection mode 302 and a tracking mode 304. During the detection mode 302, the device is detected in the x-ray images, for example, using a Hough forest algorithm, such as described in Hatt, Charles R., Michael A. Speidel, and Amish N. Raval. "Hough Forests for Real-Time, Automatic Device Localization in Fluoroscopic Images: Application to TAVR." Medical Image Computing and Computer-Assisted Intervention—MICCAI 2015. Springer International Publishing, 2015. 307-314. At process block 306, the Hough forest algorithm can be used to estimate device position, pitch, and yaw from two simultaneous x-ray images. This initial estimation provided by the Hough Forest detector is then further refined using an optimization routine at process block 308 that maximizes a metric of the similarity between the measured x-ray images and forward projections of the device model.

In the tracking mode 304, the device may be expanding and/or deforming. For example, as illustrated in FIGS. 2A and 2B, the device 200 may have variable diameter along its length between its first end 202 and its second end 204. During the tracking mode 304 this variation may be parametrized by the proximal diameter at the first end 202 and the distal diameter at the second end 204. At process block 310, subjecting the acquired data to an optimization routine yields position, pitch, yaw, roll, and the two diameters.

Figure 4:
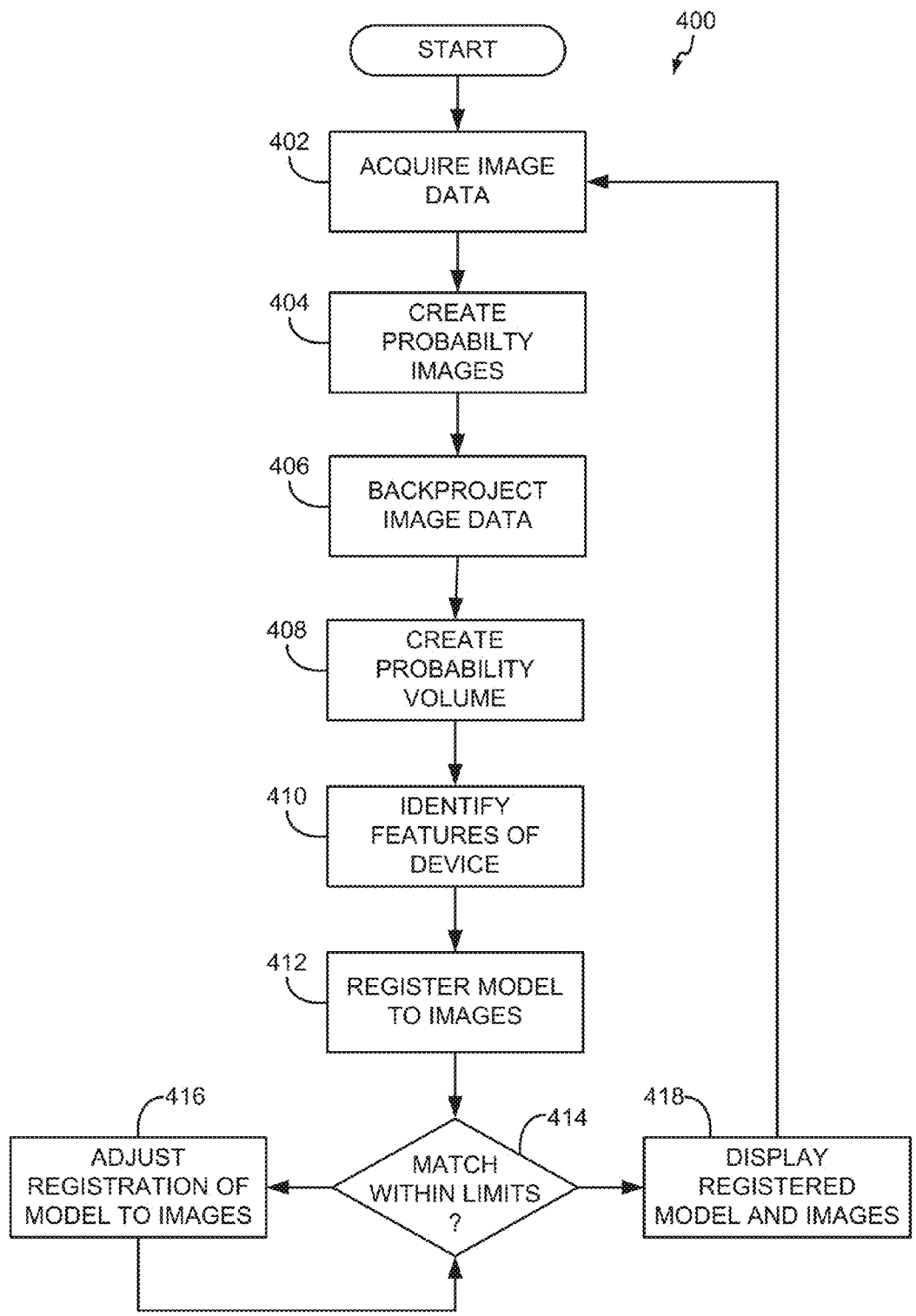
FIG. 4 is a flow chart setting forth further detailed examples of steps for tracking a medical device in accordance with the present disclosure.

Referring to FIG. 4, example steps 400 of a more detailed process for performing a 3D tracking of a dynamic device are illustrated. At process block 402, image data is acquired using an x-ray imaging system, such as described above with respect to FIGS. 1A and 1B. In particular, imaging data is acquired as the device being tracked is guided into the patient. In particular, imaging may be performed using a first x-ray imaging system of FIGS. 1A and 1B, as well as a second x-ray imaging system of FIGS. 1A and 1B, positioned generally and preferable perpendicular to the first x-ray imaging plane of the first x-ray imaging system. As such, data acquisition at process block 402 may include simultaneous bi-plane imaging using one or more x-ray imaging systems.

At process block 404, a device "probability" image is created, for example, one probability image may be created for each x-ray view. The probability image may be a "Hough" image created by applying the Hough Forest Algorithm, or similar machine learning algorithm to identify key landmarks in the device being tracked. For example, the image data acquired at process block 402 is analyzed to identify bright spots that indicate the location of the a specific portion of the device being tracked (e.g., a tip or distal end and a tail or proximal end).

In particular, the Hough Forrest Algorithm is a specific type of random forest that is designed for object detection. A random forest is a collection of decision trees that perform classification and/or regression. The Hough Forrest Algorithm may take image data as input and simultaneously performs both classification to determine if the image data is it part of an object and regression to determine the location of the object. The term Hough comes from the idea that each set of image data that is input (i.e., an image patch) is classified as part of the object and votes for the object center. Votes are added in an accumulator image and peaks are considered as object detection hypotheses. In the above-described creation of the "Hough" image at process block 404, the Hough Forest Algorithm locates landmarks, such as a tip and tail of a catheter.

Figure 5:
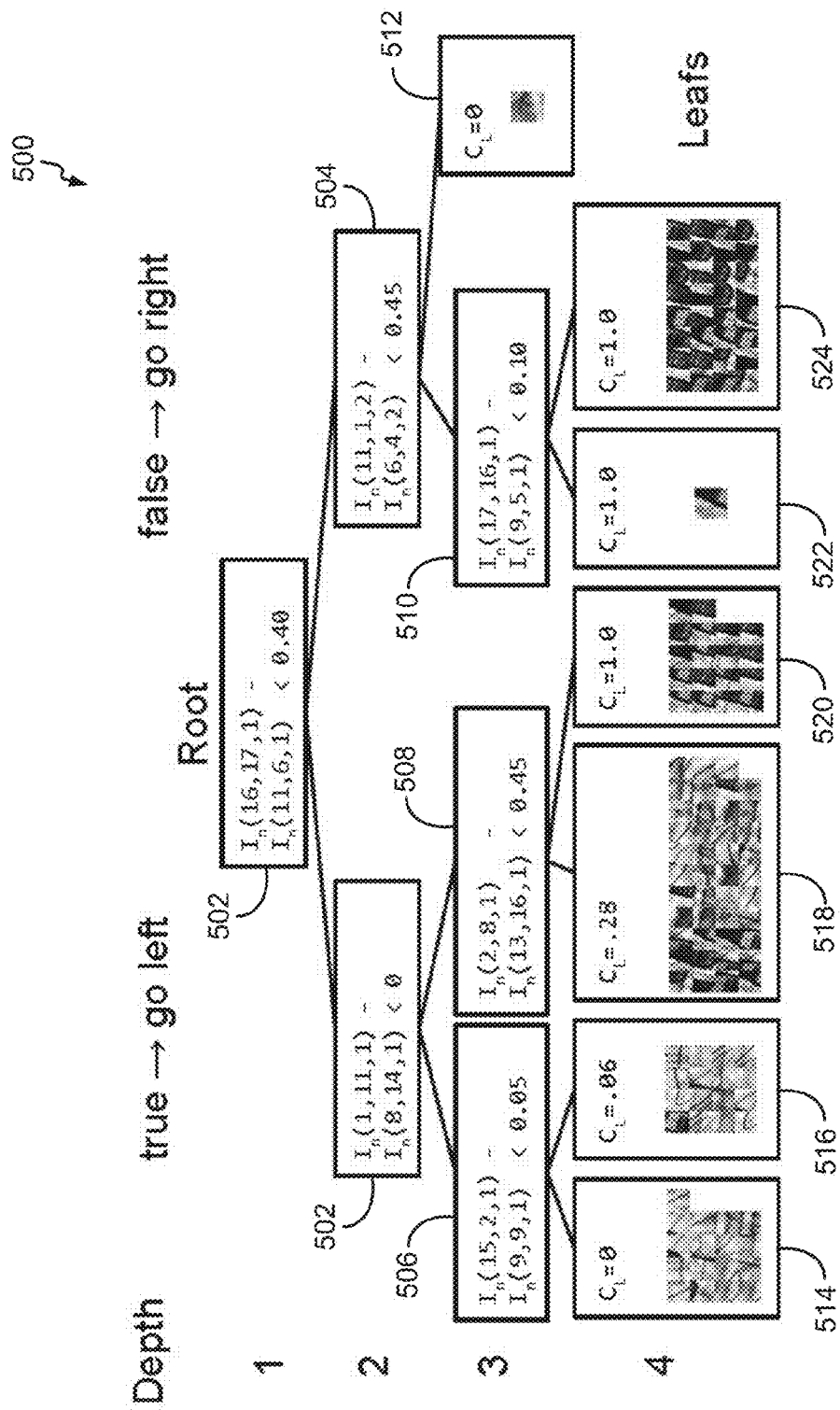
FIG. 5 is a schematic illustration of a process for detecting a device in accordance with the present disclosure.

More particularly, referring to FIG. 5, the Hough Forest Algorithm provides a framework 500 for creating a decision tree that locates the desired landmarks. A decision tree is an acyclic directed graph where each node contains a single input edge (except the root node) and two output edges (except the terminal nodes). During testing, data is input into the root node, and rules based on binary tests or features determine which edge to travel down. For image patches, these binary tests typically encode patch appearance. Eventually the data will arrive at a terminal "leaf" node. The leaf node contains data, learned during training, about how to classify (or regress) the input data. Each tree is trained by computing a set of binary tests on labeled training data, which are used to establish splitting rules. The splitting rules are chosen to maximize class discrimination at each node. In accordance with the present disclosure, binary pixel comparison tests may be used due to their computational efficiency. Multi-channel image patches can then be used as input data, where a channel can be the raw pixel intensities or some operation computed on the intensities, for example gradient magnitude, blobness, filter, or the like. For each multi-channel input training patch, $I_n$, a set of K binary tests can be computed as follows:

$$F_{k,n}(p_k,q_k,r_k,s_k,\tau_k,z_k)=I_n(p_k,q_k,z_k)-I_n(r_k,s_k,z_k)<\tau_k \quad (1);$$

where (p,q) and (r,s) are patch pixel coordinates, r is a threshold used for detecting varying contrast, and z is the channel index. Examples of image channels may include image intensity, the x-gradient, and the y-gradient. Each channel of each patch may be normalized to have a range of $$1(I_z(u,v) = \frac{I_z(u,v)}{\max(I_z) - \min(I_z)},$$

$I_z$ is he patch for channel z).

Training begins by inputting a K×N training matrix with N training patches and K tests into the root node 502. For classification, a metric is computed for each test k over all samples. In one example, the metric used for classification is the information gain:

$$G_k^c = H(S) - \frac{|S_1|}{|S|}H(S_1) - \frac{|S_0|}{|S|}H(S_0); \quad (2)$$

$$H(S) = -\sum_{c \in C} p(c)\log(p(c)); \quad (3)$$

where S is the entire set of training data, $S_0$ is the set of training data where $F_k$ is false and $S_1$ is the set of training data where $F_k$ is true, and H(S) is the Shannon entropy over all classes (device or background) in the set S.

Alternatively, for regression of continuous variables, the metric is:

$$G_k^r=|S|\text{var}(S)-|S_1|\text{var}(S_1)-|S_0|\text{var}(S_0) \quad (4);$$

where var(S) is the variance of continuous data describing the device orientation or offset vectors within each set (non-device patches may be ignored for this calculation).

A random decision may made at each node 504-512 on which attribute to base the splitting rule on class, offsets, or device orientation, for example. If the offsets are chosen, a random choice about which offsets to regress relative to the landmarks is made. The test that gives the maximum value of $G_k^c$ or $G_k^r$ is stored as the splitting rule for that node, and the training data is passed onto the left or right child node according to the splitting rule. The same process is completed until a maximum tree depth D is reached or all of the samples in a node belong to the background class. The terminal node 514-524 is termed a "leaf" node, and it stores the class labels and offsets associated with all of the training data that arrived at that node. In order to speed up run-time, offsets in each leaf node may be partitioned into clusters using k-means and the cluster means replace the original offsets. For example, 16 partitions or the like may be used.

Thus, referring again to FIG. 4, after image data is acquired at process block 402, at process block 404, a new image patch centered on $(u_p,v_p)$ is fed into the root node of each tree and traverses the tree according to the splitting rules established during training. When it arrives at a leaf node, each offset $(u_o,v_o)$ in the leaf node votes for the device parts in the Hough image accordingly:

$$I_H(u_H, v_H) \rightarrow I_H(u_H, v_H) + \frac{C_L}{|D_L|}; \qquad (5)$$

where $(u_H,v_H)=(u_p,v_p)+(u_o,v_o)$, $C_L$ is the proportion of device samples in the leaf node, and $|D_L|$ is the number of offsets in the leaf node. This process is then repeated at every patch and for every tree in the Hough Forest Algorithm.

The final $I_H$ is blurred with a gaussian kernel and peaks are classified as a given landmark, for example, tip and tail, detection hypotheses. The Hough Forrest Algorithm input patches can be sampled densely at random locations or sparsely at salient key-points. In some situations, device detection may be faster and more reliable using densely sampled patches at random locations. The final $I_H$ can be considered as a device location probability image.

Once the probability images are created, the images for each imaging plane are backprojected into the imaging volume at process block 406. The respective backprojected data can be multiplied by each other at process block 408 to create probability volume, $V_H$. The probability volume can be analyzed at process block 410 to identify volumetric bright regions that indicate the location of the landmarks identified in the probability images (such as the tail and tip in the above example) in 3D, which in turn gives the 3D position and orientation of the device. Accurate spatial calibration of the imaging planes (such as accurate location information about the C-arms of the imaging systems described above with respect to FIGS. 1A and 1B) provides proper spatial registration. This information can be streamed from x-ray imaging system or directly measured with as calibration device.

A probability volume peak may be considered a valid hypothesis if it meets a predetermined criteria. In one non-limiting example, the predetermined criteria may be to have $>0.8*\max(V_H)$ following non-maximum suppression. A predetermined number of top hypothesis may be kept. For example, the top 10 peaks may be retained as part hypotheses, but in practice usually only a few peaks survive the first criteria. In the above-described, non-limiting example, all L (tail) and M (tip) hypotheses may be combined to form L×M tip-tail pair hypotheses.

Next, unfeasible pair hypotheses should be removed. This may be done, for example, by creating distance and orientation matrices, and removing pair hypotheses that falls outside of the ranges of distance and orientation seen in the training datasets. Remaining hypotheses are then given a score, for example, such as $S_{lm}=V_{H_l}(u_l,v_l)V_{H_m}(u_m,v_m)$. The pair with the highest score is selected as the detected device to thereby provide the probability image.

Once the initial position and orientation of the device is found, this information is used to initialize the tracking algorithm at process block 412. Namely, at decision block 414, the registered model and images are reviewed against predetermined tolerance for match and, if outside the tolerance, the registration is adjusted at process block 146. Thus, the predetermined tolerance is a metric that determines when the exploration of the search space is complete. For example, the process may seek an optimization that maximizes a metric of the similarity between the measured x-ray images and forward projections of the device model. Regardless of the particular criteria reflected by the predetermined tolerance, if the match is within the predetermined tolerance, the registered model and images are displayed at process block 418 and the process iterates. That is, at process block 418, images are displayed of the subject and deformable medical device arranged within the subject based on the position and shape of the deformable medical device within the subject reflected by the match at decision block 414.

More particularly, a dynamic or deformable device changes shape and deforms as it is deployed. Similar to object tracking, where small frame-to-frame object displacements allow optimization-based methods to find the new pose of an object based on the pose from the prior frame, the current deformation at each frame can be estimated using the deformation result obtained from the previous frame. This can be accomplished by comparing numerical forward projections of a deformable 3D valve model to the measured 2D x-ray image(s).

Consider, for example, the above described expandable frame 200 of a TAVR valve illustrated in FIGS. 2A and 2B. For each frame period, the valve model position, orientation, and deployment diameter can be iteratively adjusted until the similarity between the forward projection and x-ray image is maximized or within a desired constraint. As a non-limiting example, the expandable frame may be modeled as a point cloud undergoing radial deformation that varies along the axis 206 extending between the first end 202 and the second end 204, in addition to rigid motion. For discussion purposes, a simple cost function may be considered as:

$$F_C = \Sigma_n \Sigma_j I_n(P_n \cdot T_n T_\phi \cdot D(x_j, d, s)) \qquad (6);$$

where $I_n$ is the measured x-ray image from the nth C-arm (n=2 for bi-plane x-ray), $P_n$ is the P-matrix defining the projection geometry of the nth C-arm, $T_n$ is the matrix defining the rigid transform of the nth C-arm, $T_\phi$ is the matrix defining the rigid transform of the valve according to the vector $\phi$, and D( ) is a vector-valued function that deforms a point $x_j$ on the 3D valve model according to the parameters d and s. Thus, these may be used, collectively, as deformation parameters. Alternatively, vector $\phi$ may be a vector of values, defining pitch, roll, and yaw in x,y,z. Similarly, d and s can be put into a vector, whereby equation (6) would include a vector for the deformable or non-rigid parameters and a vector for the rigid parameters.

Figure 6:
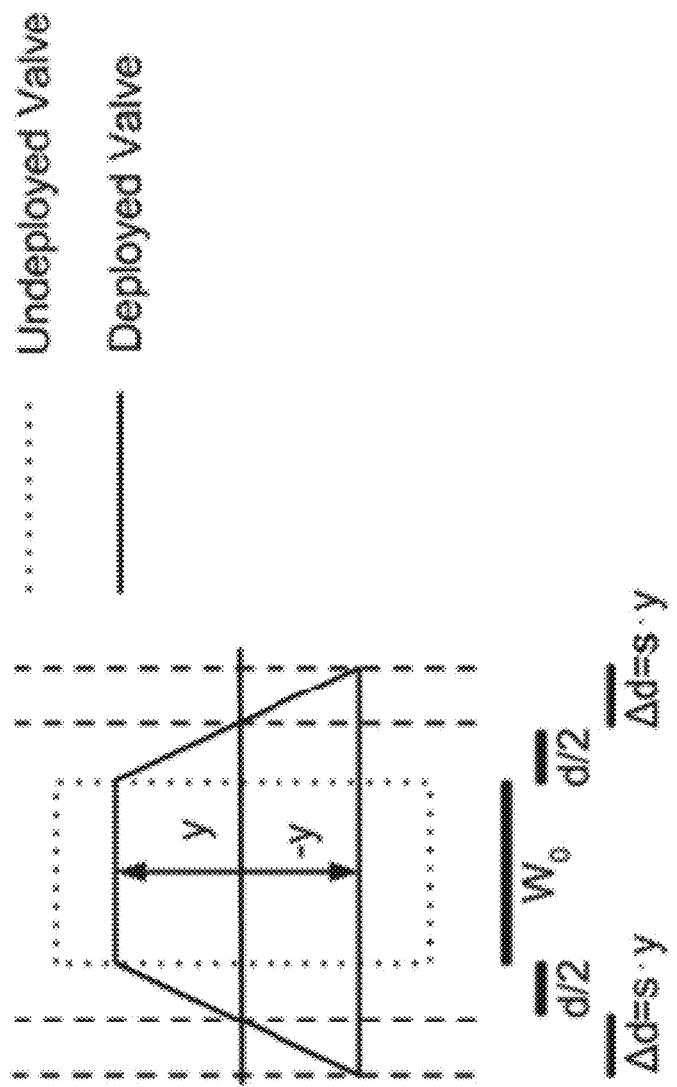
FIG. 6 is a schematic illustration of a model for a deformable medical device in accordance with the present disclosure.

Specifically, referring to FIG. 6, the parameters d and s are illustrated. It was observed from clinical datasets that, during deployment, the valve starts off shaped as a cylinder in FIG. 2A with diameter $W_0$, expands into the shape of a truncated cone as illustrated in FIG. 2B, and is finally deployed as a cylinder. Based on this observation, the deformation can be parameterized with an incremental change in diameter d, as well as an additional deformation component that varies along the central axis 206 (y-axis). The deformation component, $\Delta d$, may be assumed to vary linearly with distance y along the valve axis. Therefore, the deformation component, $\Delta d$, may be parameterized by a slope s, such that $\Delta d = sy$. The distance of each model point from the central axis of the valve is $(W_0+d)/2+sy$.

EXAMPLE

The above-described systems and methods were evaluated in a simulation study where the underlying valve geometry was exactly known. Digitally reconstructed radiographs (DRRs) of the expanding valve were generated in two bi-plane views (RAO 0/CRA 0, RAO 90/CRA 0) using a "splatting" method. The rate of valve expansion and deformation was adjusted to visually match TAVR procedures observed clinically. Spatially correlated noise (sigma=0.53 pixels) was added to the images to achieve varying signal-difference-to-noise ratios (SDNR=2,5,10,20, 50) representative of fluoro- and cine-mode imaging of an Edwards Sapien valve on a flat panel cardiac angiographic x-ray system. In the process, 20 image sequences with 50 frames of valve deployment were simulated at each noise level. To simulate motion of the prosthetic valve due to a beating heart, periodic motion was added to the model during the simulation, with 2.5 degree amplitudes for all pitch and roll, a 1 degree amplitude for yaw, 1.0 mm shifts for all translations, and a period of 1 second. The s parameter started out at 0, ramped up to a random peak value during the middle of the sequence, and then ramped back down to 0 at the end.

To isolate the performance of the pose estimation algorithm itself, the same general valve model was employed during pose estimation, except that the model struts were reduced to their 3D centerlines. The frame-to-frame expansion/deformation behavior was unknown to the pose estimation algorithm, but the model was allowed to deform with the same degrees of freedom. The relative geometry of the two bi-plane views was considered accurate; thus, assuming accurate C-arm calibration. The first frame of tracking was initialized with the known ground truth.

Simulated bi-plane x-ray views of the valve and the corresponding 3D reconstruction of the valve was evaluated in comparison to the ground truth, for an image frame with SDNR=5. The target registration error (TRE) for each frame period was calculated as the root-mean-squared difference between the corresponding true and pose-estimated positions of all points representing peaks and valleys on the sine curves used to model the valve. Histograms of the TREs per frame for each noise level are shown at 700 in FIG. 7, along with the median and the 90th percentile at 702 and 704, respectively.

Figure 7:
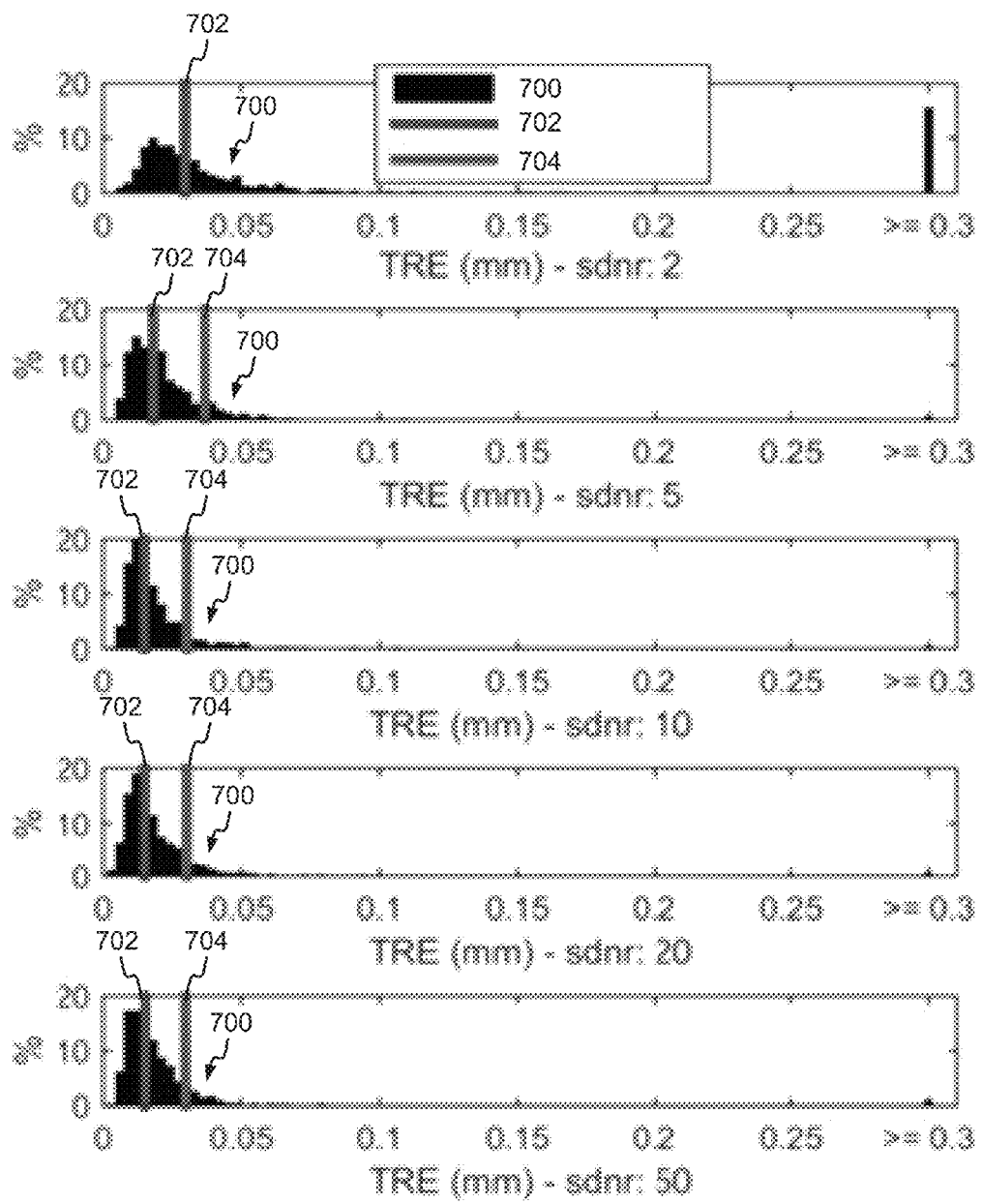
FIG. 7 is a set of graphs showing experimental results created by applying the systems and methods of the present disclosure.

As illustrated in FIG. 7, the simulation achieved a TRE of the estimated valve model of 0.93±2.6 mm for the lowest SDNR of 2. For all higher SDNRs (5 to 50) an average TRE of less than 0.04 mm with a standard deviation of less than 0.23 mm was achieved.

The estimated state of the valve deployment was also evaluated in terms of the difference between the estimated valve radius and the ground truth. The results showed a mean radius error of 0.30±1.4 mm for the lowest SDNR. For all higher SDNRs the mean radius error was less than 0.01±0.02 mm. Results of simulations indicate that the present systems and methods provide a clinically feasible resource because the TRE values were very accurate and registration rarely failed.

Therefore, a system and method is provided for frame-by-frame tracking of the 3D structure of a moving, expanding, and deforming medical device from bi-plane x-ray imaging. A 3D representation of the device registered to live 3D echocardiography or pre-acquired CT/MRI models may be used in structural heart interventions where 2D fluoroscopic guidance is ambiguous. This imaging technique may be implemented in software for use in an interventional 3D display that portrays the device registered to live 3D echo, intraprocedural CT, or pre-procedure CT/MR. It allows for frame-by-frame 3D reconstruction of a moving and expanding devices, including prosthetic valves, from simultaneous bi-plane x-ray views.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating images that track a position and shape of a deformable medical device within a subject, the method comprising:
   (i) receiving image data acquired from the subject along at least two disparate view angles, each view angle including a deformable medical device arranged in the subject;
   (ii) accessing a three-dimensional (3D) model including the deformable medical device that includes a deformation parameter for the deformable medical device;
   (iii) exploring a search space including the deformation parameter to match the image data with the 3D model within a predetermined tolerance to determine a position and shape of the deformable medical device; and
   (iv) using the image data and the position and shape of the deformable medical device determined in (iii), displaying an image of the deformable medical device arranged within the subject.

2. The method of claim 1 wherein the search space further includes at least two of a position, pitch, yaw, roll, proximal diameter, and distal diameter of the device.

3. The method of claim 1 wherein (iii) includes limiting the search space based on a priori knowledge of the deformable medical device.

4. The method of claim 3 wherein the a priori knowledge of the deformable medical device includes deformation parameters associated with an undeployed state and a deployed state.

5. The method of claim 1 wherein the deformation parameter includes at least one of model position, model orientation, and model deployment diameter and wherein (iii) includes iteratively adjusting 3D model until the predetermined tolerance between the 3D model and images created from the image data is satisfied.

6. The method of claim 1 wherein the 3D model includes a point cloud undergoing radial deformation that varies along an axis extending between a first end and a second end of the deformable medical device and varies with rigid motion.

7. The method of claim 1 wherein (iii) includes comparing a forward projection of the 3D model to images created from the image data to determine a match between the 3D model and images created from the image data that is within the predetermined tolerance.

8. The method of claim 1 wherein the predetermined tolerance is a maximization of a match between images created from the 3D model and images created from the image data.

9. The method of claim 1 wherein the deformable medical device includes a transcatheter aortic valve replacement (TAVR).

10. The method of claim 1 wherein the image data includes x-ray image data and the disparate view angles are perpendicular.

11. The method of claim 1 further comprising creating probability images from the image data that are provided to a machine learning algorithm to build the 3D model.

12. A system for generating images that track a position and shape of a medical device within a subject, the system comprising:
   an x-ray imaging system configured to acquire image data from a subject along at least two disparate view angles, each view angle including a deformable medical device arranged in the subject;
   a reconstruction system configured to reconstruct images of the subject and deformable medical device from the image data;
   a computer system configured to receive the images and explore a search space to compare the images with a dynamic three-dimensional (3D) model at least using a deformation parameter to determine a position and shape of the deformable medical device within the subject;

a display configured to display an image of the subject and deformable medical device arranged within the subject based on the position and shape of the deformable medical device within the subject determined by the computer system.

13. The system of claim 12 wherein dynamic 3D model is configured to assume different states expansion or deformation.

14. The system of claim 13 wherein the states of expansion or deformation are defined by a limited set of parameters that are included in the search space.

15. The system of claim 14 wherein the search space includes position, pitch, yaw, roll, proximal diameter, and distal diameter of the deformable medical device.

16. The system of claim 12 wherein the computer system is configured to comparing forward projections of the dynamic 3D model with and images.

17. A system for generating images that track a position and shape of a medical device within a subject, the system comprising:

an image processing system configured to:
(i) receive image data acquired from the subject along at least two disparate view angles, each view angle including the medical device;
(ii) access a three-dimensional (3D) model including the medical device that includes a deformation parameter for the medical device;
(iii) explore a search space including the deformation parameter to match the image data with a forward-projection of the 3D model within a predetermined tolerance to determine a position and shape of the medical device; and
(iv) using the image data and the position and shape of the medical device determined in (iii), display an image of the medical device arranged within the subject.

18. The system of claim 17 wherein the 3D model includes a point cloud undergoing radial deformation that varies along an axis extending between a first end and a second end of the deformable medical device and varies with rigid motion.

19. The system of claim 17 wherein the search space further includes at least two of a position, pitch, yaw, roll, proximal diameter, and distal diameter of the device.

20. The system of claim 17 wherein the deformation parameter includes at least one of model position, model orientation, and model deployment diameter and wherein (iii) includes iteratively adjusting 3D model until the predetermined tolerance between the 3D model and images created from the image data is satisfied.

* * * * *